(12) United States Patent
Shaker et al.

(10) Patent No.: US 11,938,332 B2
(45) Date of Patent: Mar. 26, 2024

(54) METHOD TO PROVIDE COMPUTATIONAL ANALYSIS AND FEEDBACK DURING A CARDIAC RESCUE

(71) Applicant: ALTRIX MEDICAL, INC., Centreville, VA (US)

(72) Inventors: Matthew Robert Shaker, Centreville, VA (US); Daniel Fleck, Potomac, MD (US)

(73) Assignee: Altrix Medical, Inc., Centreville, VA (US)

( * ) Notice: Subject to any disclaimer, the term of this patent is extended or adjusted under 35 U.S.C. 154(b) by 289 days.

(21) Appl. No.: 17/535,118

(22) Filed: Nov. 24, 2021

(65) Prior Publication Data

US 2023/0123055 A1    Apr. 20, 2023

Related U.S. Application Data

(60) Provisional application No. 63/257,548, filed on Oct. 19, 2021.

(51) Int. Cl.
| | |
|---|---|
| A61H 31/00 | (2006.01) |
| A61B 5/33 | (2021.01) |
| A61B 5/332 | (2021.01) |
| A61B 5/339 | (2021.01) |
| A61N 1/39 | (2006.01) |
| A61B 5/00 | (2006.01) |

(52) U.S. Cl.
CPC ............ *A61N 1/39044* (2017.08); *A61B 5/33* (2021.01); *A61B 5/332* (2021.01); *A61B 5/339* (2021.01); *A61H 31/005* (2013.01); *A61B 5/0006* (2013.01); *A61B 5/0077* (2013.01)

(58) Field of Classification Search
None
See application file for complete search history.

(56) References Cited

U.S. PATENT DOCUMENTS

| | | |
|---|---|---|
| 6,321,113 B1 | 11/2001 | Parker et al. |
| 7,262,747 B2 | 8/2007 | Ebersole et al. |

(Continued)

OTHER PUBLICATIONS

Digna M González-Otero, et al., Additive Model to Evaluate the Accuracy of Chest Compression, Feedback Systems in Moving Vehicles, Computing in Cardiology 2016; vol. 43 ISSN: 2325-887X DOI: 10.22489/CinC.2016.021-218, Bilbao (Spain).

(Continued)

*Primary Examiner* — Kennedy Schaetzle
(74) *Attorney, Agent, or Firm* — Louis Ventre, Jr.

(57) ABSTRACT

A method to provide feedback, coaching, and ECG analysis during a cardiac event. A rescuer would typically be attempting cardiopulmonary resuscitation (CPR) and/or administering an electrical shock from a defibrillator and/or collecting electrocardiogram (ECG) data. The method includes a step of providing a data-generation device (e.g., a camera) and computing components. The computer is used to calculate distances on the fly using data generated by the data-generation device, such as a camera, that may be in motion. The method uses the computer to calculate movement of the chest of a patient and to assess outcomes. When CPR contaminates an ECG, the computer removes the unwanted contamination so that proper guidance to the rescuer can be delivered during CPR.

20 Claims, 9 Drawing Sheets

(56) References Cited

U.S. PATENT DOCUMENTS

| | | |
|---|---|---|
| 8,979,764 B2 | 3/2015 | Elghazzawi et al. |
| 9,026,147 B2 | 5/2015 | Galvin et al. |
| 9,576,502 B2 | 2/2017 | Griesser et al. |
| 10,335,346 B2 * | 7/2019 | Centen .................. A61B 5/113 |
| 10,335,574 B2 | 7/2019 | Tegg et al. |
| 10,335,604 B2 | 7/2019 | Gehman et al. |
| 11,213,454 B1 * | 1/2022 | Shaker ................. A61H 31/007 |
| 2004/0015191 A1 | 1/2004 | Otman et al. |
| 2008/0312565 A1 | 12/2008 | Celik-Butler et al. |
| 2011/0040217 A1 | 2/2011 | Centen |
| 2012/0136286 A1 | 5/2012 | Nova et al. |
| 2012/0184882 A1 | 7/2012 | Totman et al. |
| 2014/0066822 A1 | 3/2014 | Freeman |
| 2014/0342331 A1 | 11/2014 | Freeman |
| 2015/0087919 A1 | 3/2015 | Johnson et al. |
| 2015/0164417 A1 | 6/2015 | Tupin, Jr. |
| 2015/0179219 A1 | 6/2015 | Gao et al. |
| 2015/0351647 A1 | 12/2015 | Dantu et al. |
| 2016/0128626 A1 | 5/2016 | Johnson et al. |
| 2016/0143804 A1 | 5/2016 | Nilsson et al. |
| 2017/0105898 A1 | 4/2017 | Taylor et al. |
| 2017/0156977 A1 | 6/2017 | Walden et al. |
| 2017/0181925 A1 | 6/2017 | Oppenheimer |
| 2017/0196767 A1 | 7/2017 | Cox et al. |
| 2017/0273864 A1 | 9/2017 | Kaufman et al. |
| 2017/0281461 A1 | 10/2017 | Kokubo et al. |
| 2018/0040255 A1 | 2/2018 | Freeman |
| 2018/0092802 A1 | 4/2018 | Giacometti et al. |
| 2018/0147113 A1 | 5/2018 | Dellimore et al. |
| 2018/0174489 A1 | 6/2018 | Kiran et al. |
| 2019/0066538 A1 | 2/2019 | Chao et al. |
| 2019/0133879 A1 | 5/2019 | Djajadiningrat |
| 2019/0209871 A1 | 7/2019 | O'Brien et al. |
| 2019/0257644 A1 | 8/2019 | Hillebrand |
| 2020/0000679 A1 | 1/2020 | Oppenheimer |
| 2020/0000680 A1 | 1/2020 | Silver et al. |
| 2020/0096319 A1 | 3/2020 | Botero Rosas et al. |
| 2021/0183402 A1 | 6/2021 | Bharitkar et al. |

OTHER PUBLICATIONS

Sofía Ruiz De Gauna, et al., Feedback on the Rate and Depth of Chest Compressions during Cardiopulmonary Resuscitation Using Only Accelerometers, PLOS One, DOI:10.1371/journal.pone. 0150139 Mar. 1, 2016, published online at https://www.ncbi.nlm.nih.gov/pmc/articles/PMC4773040/ .

\* cited by examiner

METHOD TO PROVIDE COMPUTATIONAL ANALYSIS AND FEEDBACK DURING A CARDIAC RESCUE

CROSS-REFERENCE TO RELATED APPLICATION

This application claims the benefit of U.S. Provisional Application No. 63/257,548, filed 19 Oct. 2021, which is hereby incorporated by reference herein.

TECHNICAL FIELD

In the field of sensing body condition and electrical application for heart-related emergencies, a method is disclosed for improving cardiac rescue utilizing real time feedback, the method also providing tools to avoid a detrimental practice of pausing cardiopulmonary resuscitation (CPR) when collecting electrocardiogram (ECG) data.

BACKGROUND ART

Chest compression fraction (CCF), chest compression rate, chest compression depth, and minimizing residual leaning on a patient's chest are considered major components of high-quality CPR. CCF is defined as the proportion of time that chest compressions are performed during a cardiac arrest. However, pauses in administering CPR to a person in cardiac distress are often necessary to assess that person's condition using an ECG. Recent studies have shown that such pauses are correlated with a decreased survival rate for such person or victim. Conversely, the ability to collect and analyze a cardiac arrest victim's ECG without pausing CPR is correlated with higher CCF and improved outcomes.

CPR is an emergency procedure that can help save a person's life if their heart stops. CPR mechanically forces the heart to pump blood to the brain, the lungs and to other parts of the body and attempts to restore a return to spontaneous circulation (ROSC).

The American Heart Association recommends CCF greater than 80%, compression rates between compression rates of 100-120 per minute, and compression depth of at least 50 mm (2 inches) in adults and at least ⅓ of the anterior-posterior dimension of the chest in infants and children.

ECG is a test procedure that measures the heart's electrical activity each time it beats. With each beat, an electrical impulse travels through the heart. This wave causes the muscle to squeeze and pump blood from the heart. An ECG helps diagnose problems with a person's heart.

Someone in cardiac arrest is experiencing an arrhythmia and should receive CPR as quickly as possible. Arrhythmias are essentially irregular heartbeats. Two types, ventricular fibrillation (VF) and pulseless ventricular tachycardia (pulseless v-tach), can sometimes be reversed using an electrical shock delivered to the heart by a defibrillator if treated promptly, thus giving the heart the opportunity to resume normal contractions in pumping blood (i.e., ROSC). However, detecting these shockable rhythms requires an ECG be taken while CPR is paused or that the ECG tool include a method to redact CPR artifacts from the ECG.

A further challenge with defibrillation is that the electrical shock must be administered very soon after the onset of the arrhythmia. There is not much time to do this since the survival rate decreases by about 10% for each minute the person is in cardiac arrest. After about 10 minutes the rate of survival for sudden cardiac arrest (SCA) victims averages less than 2%.

High quality CPR and defibrillation are considered essential elements of first response that can be provided by bystanders or trained first responders, such as emergency medical technicians (EMT). Having an ability to assess and adjust the quality of cardiac first response in real time while also minimizing pauses in CPR contributes to better patient outcomes. In addition, providing after action information on a treatment event can improve the survival rates for future persons in cardiac distress by helping responders to understand opportunities for improvement.

The method builds upon the method disclosed in U.S. application Ser. No. 17/339,979, filed 5 Jun. 2021, which is hereby incorporated by reference herein in its entirety. The added scope includes obtaining the ECG and redacting the CPR artifacts from the ECG signal. By knowing the CPR frequency (acquired by the method in 17339979, namely operating the computer for calculation of a movement of an article over time relative to a stationary feature) the CPR frequency is known and can be removed from the ECG signal.

The added scope further includes employing remote photoplethysmography (RPPG) to calculate heart rate, using a time-of-flight sensor as a data generation device, and calculating End Tidal CO2 (ETCO2) by analyzing any variations in the infrared frequency of exhalations from the cardiac victim.

SUMMARY OF INVENTION

A method to provide feedback, coaching, and ECG analysis during a cardiac event. The method determines a depth and rate of cardiopulmonary resuscitation (CPR) compressions. These compressions are administered by a rescuer or by an automated CPR device. The method may include steps to simultaneously produce an electrocardiogram, to remove the contaminating frequency signal from a CPR frequency signal, and to assess CPR quality and patient outcomes in real-time.

The method includes steps of providing a computer, a stationary feature, a data-generation device, and an article; configuring the computer to receive data from the data-generation device; locating the data-generation device to view the stationary feature and the article; configuring the stationary feature as a fixed reference; configuring the article to be movable with a chest of the person in cardiac distress; viewing the article and the stationary feature with the data-generation device to generate the data sent to the computer; and operating the computer for calculation of a movement of the article over time relative to the stationary feature, said calculation comprising a determination of a difference between a first distance and a second distance, said first distance defined by a first space between the data-generation device and the stationary feature, said second distance defined by a second space between the article and the data-generation device.

The method may further include steps of: selecting the stationary feature to comprise a defined plane of a surface upon which the person in cardiac distress is lying; including a time-of-flight sensor in the data-generation device and configuring the data-generation device to view the article and the defined plane; the data-generation device further includes a camera, which views the article and the defined plane; and configuring the time-of-flight sensor to project a virtual grid over the article, the person in cardiac distress and the defined plane. Optionally, the time-of-flight sensor is used to identify the defined plane by computing a two-dimensional surface, which corresponds most closely to an outer edge of the virtual grid;

The method may further include steps of: configuring the stationary feature with a shape or image having a known dimension and calculating the first distance between the data-generation device and the stationary feature using the data and the known dimension of the stationary feature.

The method may further include steps of: configuring the article with a shape or image having a second known dimension; and calculating the second distance between the data-generation device and the article using the data and the second known dimension.

The method may further include steps of: recording an electrocardiogram from the operation of a defibrillator on the person in cardiac distress; recording the data from the data-generation device on a rate of cardiopulmonary resuscitation and depth of chest compression by the rescuer.

The method may further include steps of: providing a cuing device; configuring the cuing device to send guidance to the rescuer; connecting the cuing device to the computer; and activating the cuing device to send a recommendation to the rescuer when an adjustment of an action of the rescuer is suggested by the computer in treating the person in cardiac distress. Optionally, added steps involving the cuing device may include sending the recommendation selected from the group consisting of a visual cue and an auditory cue; and selecting the cuing device from the group consisting of a smartphone, a computer tablet, a laptop display, and a defibrillator, and augmented reality glasses either alone or paired with another device such as the cuing device or an inertial measurement unit.

The method may further include the step of defining the stationary feature to comprise a known dimension of a defibrillator.

The method may further include steps of including an inertial measurement unit in the article; connecting the inertial measurement unit to the computer wherein the computer receives motion data from the inertial measurement unit indicating a measure of acceleration of motion of the article; operating the computer to convert the motion data from the inertial measurement unit into frequency domain data through Fourier transforms; using the frequency domain data in conjunction with first data from the data-generation device to compute a maximum displacement of a chest of the person in cardiac distress; activating the cuing device to send a recommendation to the rescuer when the maximum displacement of the chest of the person in cardiac distress is computed to be inadequate.

The method may further include the step of providing a microphone configured to enable the rescuer to interact with the computer, the computer configured with artificial intelligence.

The method may further include the step of providing a transceiver configured to send and receive data from the computer and to provide interactive communication between the rescuer and an emergency call center.

The method may further include steps of: providing a defibrillator configured for interfacing with the computer.

The method may further include the step of integrating the computer into the defibrillator.

The method may further include steps of: connecting an electrocardiogram device to the person in cardiac distress using an electrode that detects an electrocardiogram data stream contaminated with cardiopulmonary resuscitation data; operating the computer to convert the data from the data-generation device to produce a CPR frequency and magnitude signal; defining a proportion of the CPR frequency and magnitude signal to remove from the electrocardiogram data stream; removing the proportion from the electrocardiogram data stream to produce a net electrocardiogram frequency and magnitude data stream.

The method may further include steps of: positioning the data-generation device to view and record changes in light absorption of the skin; and configuring the computer to utilize the data to calculate heart rate using photoplethysmography.

The method may further include the step of positioning the data-generation device to view and record changes in motion of the chest of the person in cardiac distress.

The method may further include steps of: configuring the data-generation device to receive exhalation data from the nose and mouth; and configuring the computer to calculate End Tidal CO2 (ETCO2) by analyzing any variations in the infrared frequency.

Technical Problem

Methods to improve cardiac rescue could be helpful in saving lives and lowering costs for failed treatment. It has been reported in a 2008 conference paper that each year "approximately 340,000 people die from sudden cardiac death in the United States. Estimates of costs for failed treatment and lost productive years of life amount to over $400 billion per year." Cardiac Synchronization, Charles Little, Univ. of Colorado, https://www.researchgate.net/publication/280080591.

A frequent challenge for untrained responders to a sudden cardiac arrest is helping them understand what to do, how to do it, and (sometimes as important) what not to do. Even trained first responders could find real time coaching helpful during an emergency. In fact, research has shown that variability in CPR performance results in poorer outcomes, a problem exacerbated by the fact that the quality of CPR typically diminishes over time due to rescuer fatigue.

Several recent studies have shown that synchronizing chest compressions with residual activity in the heart can lead to better outcomes for the cardiac arrest victim. For example, synchronization of chest compressions with residual systolic cardiac activity is associated with improved coronary perfusion pressures in a swine model of pseudo-pulseless electrical activity cardiac arrest.

The American Heart Association recommends that pediatric patients receive chest compressions that depress the chest at least one third the anterior-posterior diameter of the chest. Because there is currently no emergency technology to measure anterior-posterior depth, the AHA suggests approximate depths of approximately 1.5 inches (4 cm) in infants to 2 inches (5 cm) in children.

Audio and video prompts, or even 911 assisted coaching, doesn't always provide the detail needed because real time data cannot be assessed. This can be especially problematic with cardio-pulmonary resuscitation (CPR), where rate and depth of compressions are particularly important along with limiting pauses to CPR (increased CCF) and eliminating residual leaning by the rescuer.

Using existing methods for guiding proper placement of defibrillator pads on a patient can be deficient because there is no visual context in relation to the actual person in the environment nor any way to visually confirm correct pad placement.

While modern defibrillators can be programmed to detect proper pad placement by measuring resistance between the pads, there is no way to automate visual validation of correct pad placement. Visual validation would also improve delivery of CPR because it can advise on best patient position, such as lying on a hard flat surface that also minimizes any water hazard that might pose a danger when using a defibrillator.

Many existing CPR coaching devices do not effectively address leaning during CPR, which is a recognized problem. The National Institutes of Health published a report stating: "Leaning during CPR increases intrathoracic pressure, decreases coronary perfusion pressure, and decreases cardiac output and myocardial blood flow. Leaning is common during CPR."

Simultaneous electrocardiograms (ECG) taken of patients undergoing cardiopulmonary resuscitation (CPR) can lead to contamination of the CPR frequency data.

Contamination of the CPR frequency data inhibits the development of correct guidance being given to the rescuer on recommendations for defibrillation or on synchronizing chest compressions with residual activity in the heart.

Contamination of ECGs can lead to incorrect analysis of the ECG for evaluating cardiac recovery of the person being treated.

A method is needed to separate out unwanted frequency data from either the ECG frequency signals or the CPR frequency signals when simultaneous electrocardiograms (ECG) are taken of patients undergoing cardiopulmonary resuscitation (CPR).

Solution to Problem

The solution is a method that maximizes treatment efficacy using computer vision, inertial measurement unit technology, and time of flight (TOF) technology.

This maximized treatment efficacy is enhanced by knowing the CPR depth and using that to enable calculation of an estimate of the energy within the observed CPR frequency band. Such knowledge permits removal of the CPR signal while leaving some artifacts of the ECG signal that are in the same frequency band as the CPR.

The solution is a method that enables recovery of the ECG signal without some of the CPR artifacts. The ability to collect and analyze a cardiac arrest victim's ECG without pausing CPR is correlated with an increased rate of survival.

The solution is a method that enables redaction of the CPR signal from an ECG. The ability to collect and analyze a cardiac arrest victim's ECG without pausing CPR is correlated with better patient outcomes.

The solution is a method step using real time CPR recording and feedback instructing the rescuer to push harder (depth), faster (rate), when to pause for a defibrillator shock (via integration with a defibrillator), when to resume, and when to prompt the rescuer to stop leaning if residual leaning on the patient is detected during CPR.

The solution is a method step that enables use of computer vision, and data derived from hardware inertial measurement units to provide real time feedback to rescuers assisting with a cardiac arrest.

The solution is a method step that calculates End Tidal CO2 (ETCO2) by analyzing any variations in the infrared frequency of exhalations from the cardiac victim. The importance of this step is validated in part by an American Heart Association (AHA) statement in year 2019 that "physiological data during CPR that are pertinent for monitoring include invasive hemodynamic data (arterial and central venous pressures when available) and end-tidal carbon dioxide concentrations." http://ahajournals.org.

BRIEF DESCRIPTION OF DRAWINGS

The drawings illustrate the steps in preferred embodiments of the method for determining a depth and rate of cardiopulmonary resuscitation compressions administered by a rescuer according to the disclosure.

DESCRIPTION OF EMBODIMENTS

In the following description, reference is made to the accompanying drawings, which form a part hereof and which illustrate several embodiments of the present invention. The drawings and the preferred embodiments of the invention are presented with the understanding that the present invention is susceptible to changes in the sequence of steps that may be employed, unless otherwise required by the limitations stated in the step, without departing from the scope of the present invention. The drawings utilize dashed lines connecting steps to show optional steps in the method. Solid lines connecting steps are used to identify required steps.

The reference numbers in the drawings associated with the steps in the method are formatted such that: The first number is the figure in which the step is found; the next two numbers represent the claim number where that step can first be found; and the last number represents the position of the step in the claim. Thus, each number inherently discloses the figure in which it may be found and the claim where such step is first disclosed. The drawing (FIG. 9) showing components only uses the first digit in the reference number to identify the figure number in which it is found and the other numbers in each such reference number are simply unique designations.

Figure 1:
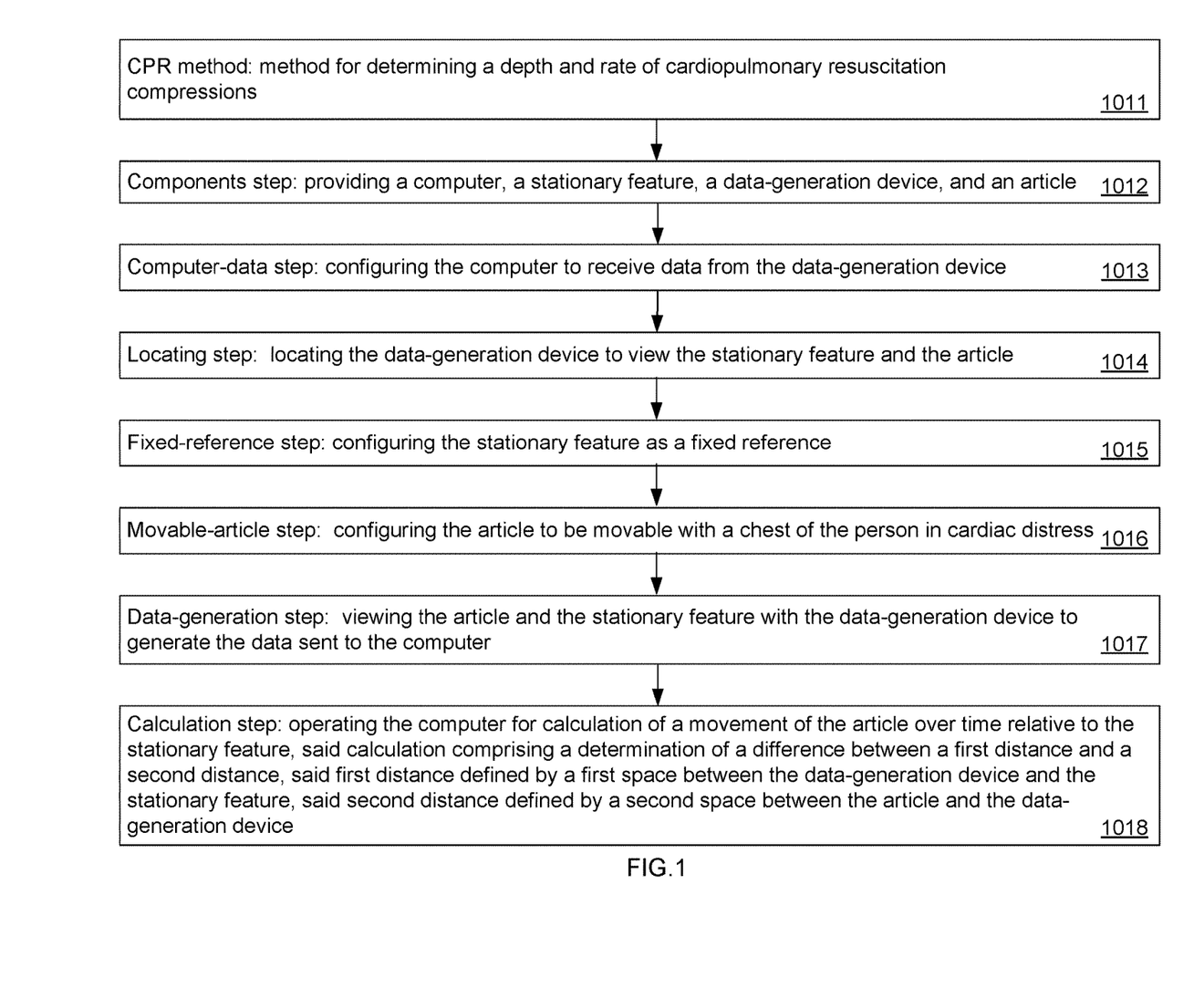
FIG. 1 is a flow chart illustrating required steps in the method.

A CPR method (1011) is disclosed. The CPR method (1011) employs a unique method for determining distances using a mobile recording device where the attributes of cardiopulmonary resuscitation can be readily determined and evaluated so that real-time computerized guidance to the rescuer may be provided, if necessary. Recording is preferably done by connection to storage in the computer (915). The CPR method (1011) is first used for determining a depth and rate of cardiopulmonary resuscitation compressions administered by a rescuer (905) to a person in cardiac distress (910). Subsequent optional steps enable redaction of CPR frequencies from the electrocardiogram frequencies to improve the evaluation of an ECG.

The CPR method (1011) includes a Components step (1012); a Computer-data step (1013); a Locating step (1014); a Fixed-reference step (1015); a Movable-article step (1016); a Data-generation step (1017); and a Calculation step (1018).

The Components step (1012) includes providing a computer (915), a stationary feature (950), a data-generation device (925), and an article (945).

The Computer-data step (1013) includes configuring the computer (915) to receive data from the data-generation device (925). Such data is preferably received via an electromagnetic signal (916).

The Locating step (1014) includes locating the data-generation device (925) to view the stationary feature (950) and the article (945).

The Fixed-reference step (1015) includes configuring the stationary feature (950) as a fixed reference. A fixed reference means, and is defined for purposes herein, as an object, an image, a dimension or a shape that is not changed in size, shape or dimension during any continuous process of data collection and preferably that remains at an unchanged position or location during said process. If there is a movement of the stationary feature (950) or data generation device, or if the position is changed, then the process starts anew with the new changed configuration.

The Movable-article step (1016) includes configuring the article (945) to be movable with a chest (911) of the person in cardiac distress (910). Acceptable configurations include glue or other attachment mechanisms for points on the chest of the person in cardiac distress (910) or the wrist or hands of the rescuer. The article (945), when in the form of a sticker, electrode, or defibrillation pad may be attached the chest of the person in cardiac distress (910).

The Data-generation step (1017) includes viewing the article (945) and the stationary feature (950) with the data-generation device (925) to generate the data sent to the computer (915). The term "viewing" is broadly defined to include more than simply detection of light in the visible spectrum. For example viewing using mechanisms may include radar, infrared, or other parts of the electromagnetic spectrum effective at detection and observation. The data referred to in this step as in all the steps is the data collected by the data-generation device (925) during any period of CPR or treatment of the person in cardiac distress (910).

The Calculation step (1018) includes operating the computer (915) for calculation of a movement of the article (945) over time relative to the stationary feature (950), said calculation comprising a determination of a difference between a first distance and a second distance, said first distance defined by a first space between the data-generation device (925) and the stationary feature (950), said second distance defined by a second space between the article (945) and the data-generation device (925).

Example Calculation

In this calculation example, the data-generation device (925) is a camera that generates data sent to the computer (915) enabling the computer to calculate the depth of chest compression during CPR. The camera uses the stationary feature (950) having a known dimension and an article (945) also having a known dimension.

In this calculation example, the calculation of the depth of chest compression is the distance that the article (945) travels in a direction orthogonal to the surface that the person in cardiac distress (910) is lying on. The direction orthogonal to the surface is termed the Z axis. The calculation performed by the computer (915) uses two frames of reference (i.e. two coordinate systems). The first frame of reference is called the world frame and the second frame is called the camera frame. The origin of the camera frame is the camera with the Z axis extending out of the lens. The origin of the world frame is preferably the stationary feature with the Z axis extending upward, the upward direction being computed using the orientation of either the article (945) or the stationary feature (950). The spaces between the camera and the article and the camera and the stationary feature are used to define the locations and derive the distances of these objects, as discussed below.

The distance to the origin of the article (945) in the camera frame and the distance to the origin of the stationary feature (950) in the camera frame are each determined by using their known dimensions. Then, using the known dimension of the stationary feature, the computer (915) utilizes a transformation matrix to rotate, scale, and translate between the camera frame and the world frame.

The computer (915) uses the transformation matrix to solve the equation for the World Frame=transformation matrix times the camera frame. Therefore, the computer (915) calculates the location of the article (945) in the world frame as equal to the product of the transformation matrix times the camera frame.

Using the location of the article (945) in the world frame, the computer (915) subtracts the Z component from the stationary feature (950) (which is zero because it is preferably set at the origin) to determine the height of the article (945) above the stationary feature (950). Measuring this distance over time gives us the compression maximum and minimum values.

This calculation example illustrates that the origin of the world frame may be present at different coordinates than the origin of the stationary feature (950). Using the origin of the stationary feature (950) as the origin in the world frame does not limit the solution to requiring use of the origin as the stationary feature (950) because this calculation derives the distance between the article (945) and the stationary feature (950) in the world frame in the Z direction.

Figure 2:
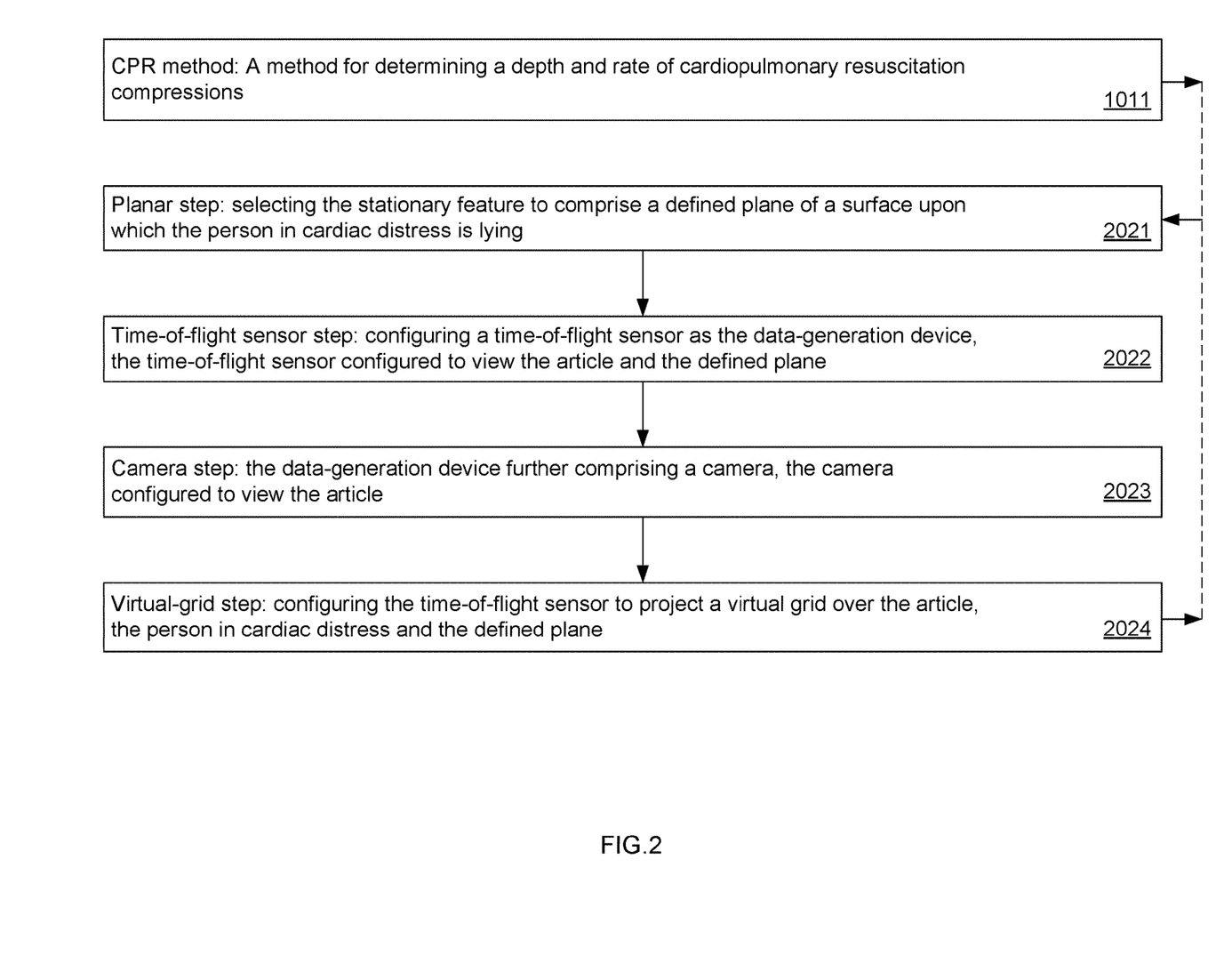
FIG. 2 is a chart illustrating optional added steps in the method.

A first set of optional steps in the CPR method (1011) includes: a Planar step (2021); a Time-of-flight-sensor step (2022); a Camera step (2023); and a Virtual-grid step (2024).

The Planar step (2021) includes selecting the stationary feature (950) to comprise a defined plane of a surface upon which the person in cardiac distress (910) is lying. As examples, the defined plane might be nearby ground, a rescue sled, or a rescue table.

The Time-of-flight-sensor step (2022) includes configuring a time-of-flight (ToF) sensor as the data-generation device where the time-of-flight sensor is configured to view the article and the defined plane. The time-of-flight sensor may be included as a separate component or part of another component. Preferably, the ToF sensor is, or is a part of, the data-generation device (925). A ToF sensor, also referred to as a time-of-flight camera, uses infrared light, typically a laser that is invisible to human eyes. The laser is used similarly to a bat's echo-location sensors. The ToF sensor determines depth and location information by emitting a light signal, which hits the subject and returns to the sensor. The time it takes to bounce back is measured and that provides depth-mapping capabilities. A ToF sensor provides an advantage as it can instantaneously and accurately measure distances to an object in a complete scene with a single laser pulse.

The Camera step (2023) includes a limitation that the data-generation device (925) further comprises a camera. The camera is configured to view the article (945).

The Virtual-grid step (2024) includes configuring the time-of-flight sensor to project a virtual grid over the article (945), the person in cardiac distress (910) and the defined plane. The virtual grid is a computer generated overlay on the field of view of the time-of-flight sensor. The time-of-flight sensor captures an image for each point on the virtual grid at which the time-of-flight sensor, acting as a directional light source illuminates the specified objects. The location and orientation of the directional light source are calibrated relative to the field of view of the time-of-flight sensor.

Other optional steps in the CPR method (1011) includes: a Defined-plane step (3031); a Known-dimension step (3041); a First-distance step (3042); a Shape step (3051); a Second-distance step (3052); an ECG step (3061); a Recording step (3062); a Cuing step (4071); a Guidance step (4072); a Recommendation step (4073); a Glasses step (4081): a Cuing-type step (4091); a Device-option step (4101); a Dimension step (5111); an Inertial step (5121); a Connecting step (5122); a Frequency step (5123); a Displacement step (5124); an Added-push step (5127); a Microphone step (6131); a Transceiver step (6141); a Shock step (6151); a Safety step (6152); an Integrating step (6161); an ECG step (7171); a CPR-frequency step (7172); a Proportion step (7173); a Redaction step (7174); a Positioning step (7180); a Skin step (7181); a Heart step (7182); a Viewing step (7191); a Chest step (7192); a Nose-and-Mouth step (8201); a Detection step (8202); a Breath step (8203); and an Infrared step (8204).

Figure 3:
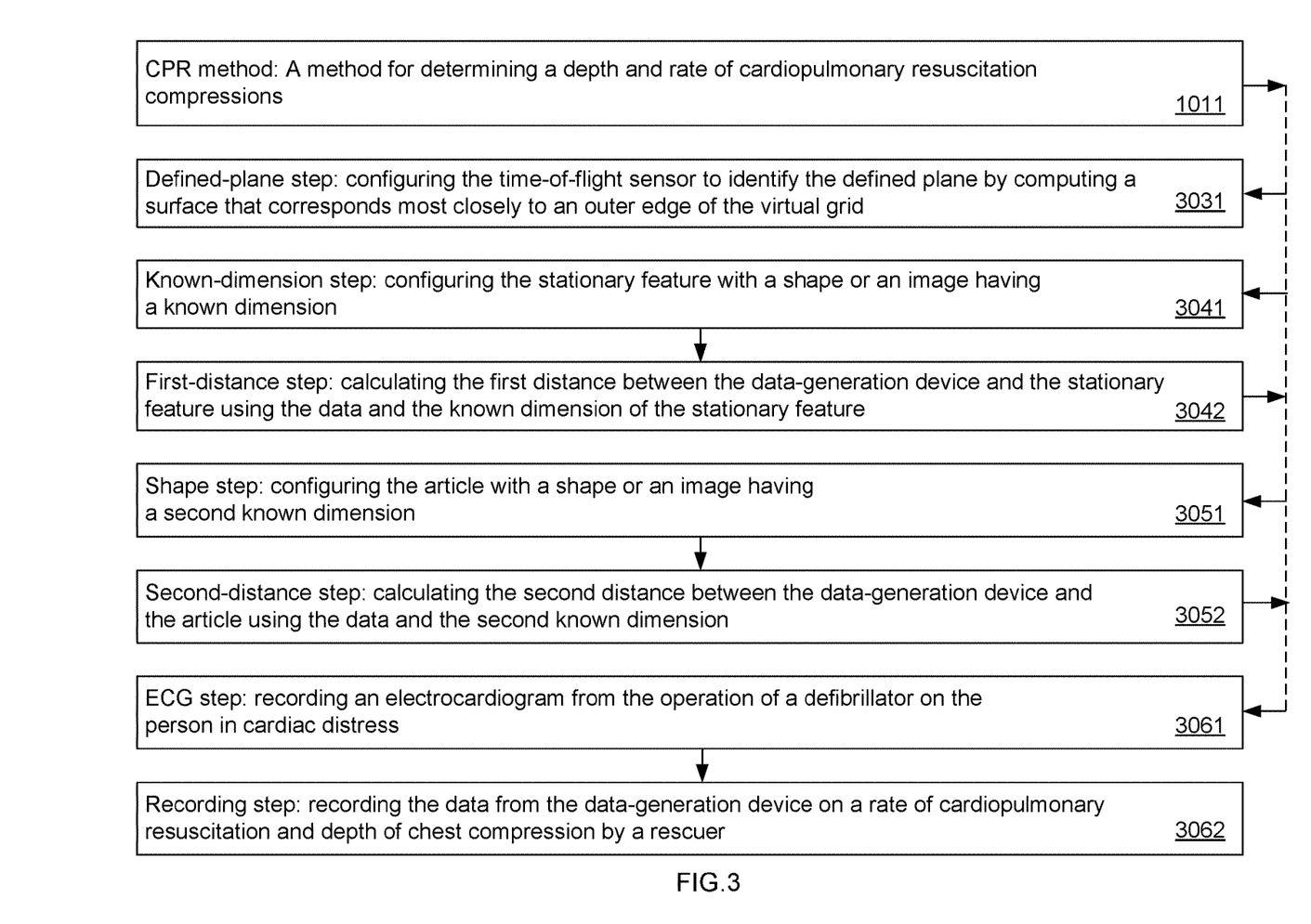
FIG. 3 is a chart illustrating optional added steps in the method.

The Defined-plane step (3031) includes configuring the time-of-flight sensor to identify the defined plane by computing the surface that corresponds most closely to an outer edge of the virtual grid. The surface is preferably a two-dimensional surface.

Known-dimension step (3041) includes configuring the stationary feature (950) with a shape or an image having a known dimension.

The First-distance step (3042) includes calculating the first distance between the data-generation device (925) and the stationary feature (950) using the data and the known dimension of the stationary feature (950). As is the case throughout this disclosure, the term "data" is the data from the data-generation device.

The Shape step (3051) includes configuring the article (945) with a shape or an image having a second known dimension. The Shape step (3051) is similar to the Known-dimension step (3041), except that The Shape step (3051) is applicable to the article (945) instead of the stationary feature (950). The article (945), may be worn or attached to the rescuer or, if in the form of a sticker, electrode, or defibrillation pad may be attached the chest of the person in cardiac distress (910).

The Second-distance step (3052) includes calculating the second distance between the data-generation device (925) and the article (945) using the data and the second known dimension.

The ECG step (3061) includes recording an electrocardiogram (ECG) from the operation of a defibrillator (955) on the person in cardiac distress (910). The recording of the ECG would typically be in the defibrillator (955) and may alternatively be in the computer (915), or may be in both the defibrillator (955) and the computer (915).

The Recording step (3062) includes recording the data from the data-generation device (925) on a rate of cardiopulmonary resuscitation (CPR) and depth of chest (911) compression by the rescuer (905). Recording may be in any storage component, located for example in computer memory in the computer (915), in the data-generation device (925) or in any other device connected to the data-generation device (925).

Figure 4:
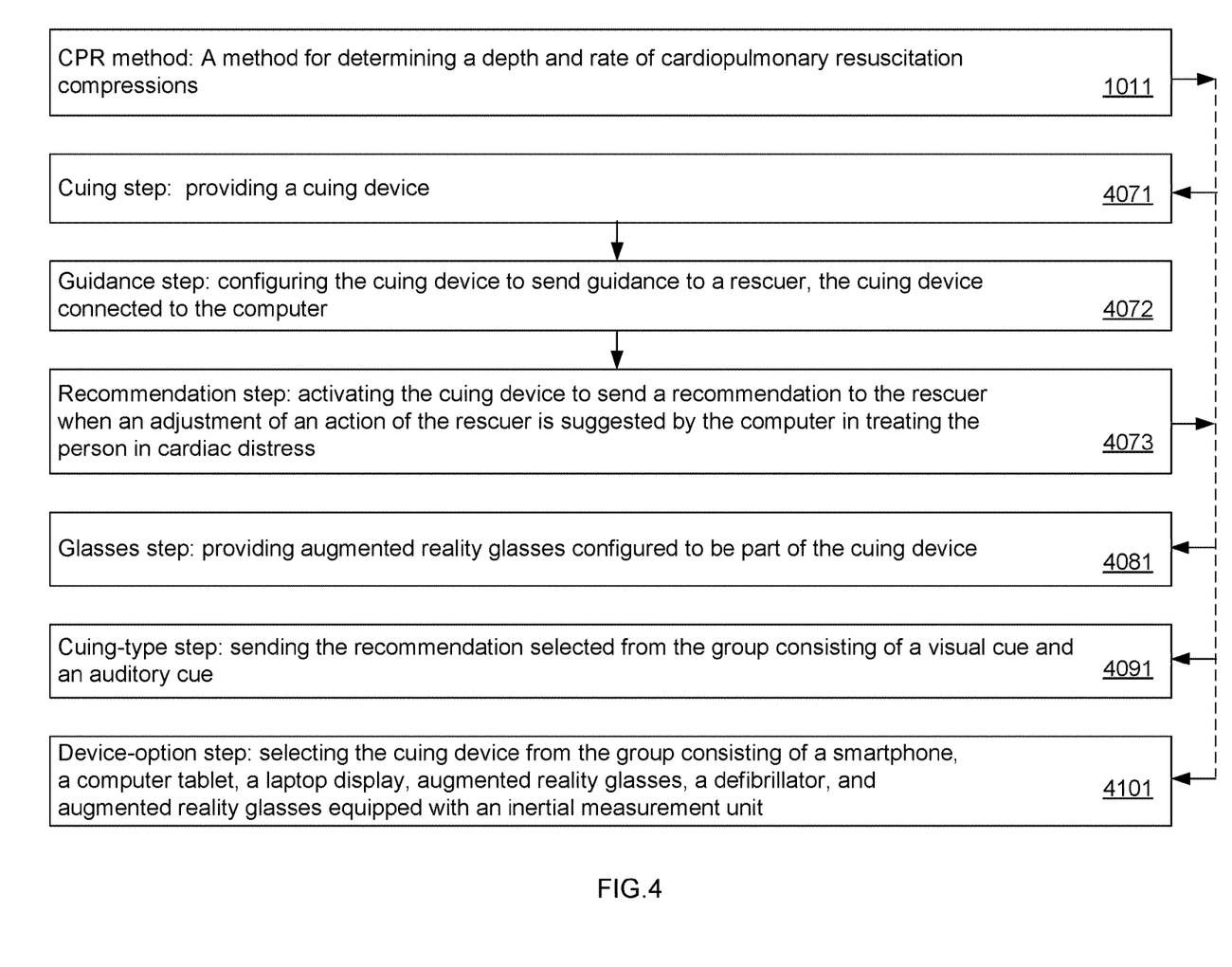
FIG. 4 is a chart illustrating optional added steps in the method.

The Cuing step (4071) includes providing a cuing device. The cuing device would typically include a computer, be built into the computer (915), or simply be connected to the computer (915), but could be a separate component activated by the computer (915). Examples of cuing devices would typically include a headphone (935), a cell phone, also known as a smart phone (961), or a pair of augmented reality glasses (960).

The Guidance step (4072) includes configuring the cuing device to send guidance to the rescuer (905), the cuing device connected to the computer (915), for example by a wireless connection.

The Recommendation step (4073) includes activating the cuing device to send a recommendation to the rescuer (905) when an adjustment of an action of the rescuer (905) is suggested by the computer (915) in treating the person in cardiac distress (910).

The Glasses step (4081) includes providing augmented reality glasses (960). The augmented reality glasses (960) may also serve as the cuing device or may be configured to be a part of the cuing device. Also, the augmented reality glasses (960) may include the computer (915).

The CPR method (1011) optionally includes using a LIDAR (Light Detection and Ranging) device as the data-generation device. The LIDAR device is configured to supply the distance to the hands or the chest (911) of the rescuer (905) who is treating the person in cardiac distress (910). Alternatively, the article (945), such as a sticker, may be attached the chest of the person in cardiac distress (910).

The Cuing-type step (4091) includes sending the recommendation selected from the group consisting of a visual cue and an auditory cue. A flashing light or a beeping signal are examples of a visual cure and an auditory cue, respectively.

The Device-option step (4101) includes selecting the cuing device from the group consisting of a smart phone (961), a computer (915) tablet, a laptop display, augmented reality glasses (960), a defibrillator (955), and augmented reality glasses (960) equipped with an inertial measurement unit.

Figure 5:
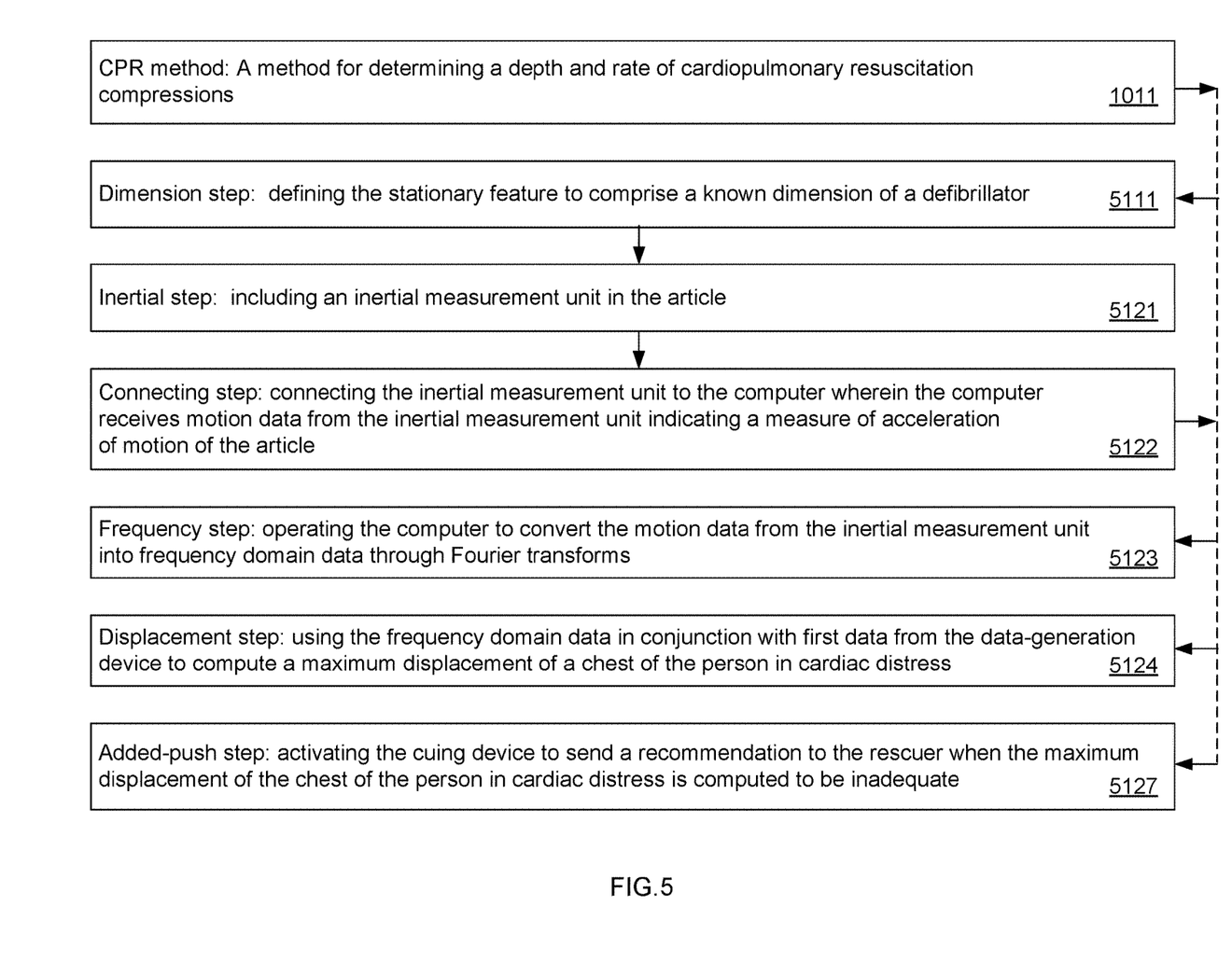
FIG. 5 is a chart illustrating optional added steps in the method.

The Dimension step (5111) includes defining the stationary feature (950) to comprise a known dimension of a defibrillator (955).

The Inertial step (5121) includes adding an inertial measurement unit (IMU) in the article (945). The inertial measurement unit (930) is a small device. One example is a match-box-sized device, typically about 1.5" by 1" and about 0.4 inches thick. With today's miniaturization capabilities, an IMU may be significantly smaller. As a non-limiting example, the inertial measurement unit (970) is a BLUETOOTH inertial measurement unit connected to the smart phone (961). BLUETOOTH is a short-range wireless technology standard that is used for exchanging data between fixed and mobile devices over short distances using UHF radio waves in the ISM bands, from 2.402 GHz to 2.48 GHz, and building personal area networks. The IMU integrates multi-axes, accelerometers, gyroscopes, and other sensors to provide estimation of an object's orientation in space. Preferably, the inertial measurement unit (930) measures 9 axes: 3 axes for acceleration, 3 for gyroscope, and 3 for magnetometer. Measurements of acceleration, angular rate, and attitude are typical data outputs. IMU inertial sensors are commonly used in dynamic motion measurements, payload platform stabilization, and antenna and camera pointing applications.

The Connecting step (5122) includes connecting the inertial measurement unit (930) to the computer (915) wherein the computer (915) receives motion data from the inertial measurement unit indicating a measure of acceleration of motion of the article (945).

The Frequency step (5123) includes operating the computer (915) to convert the motion data from the inertial measurement unit (930) into frequency domain data through Fourier transforms.

The Displacement step (5124) includes using the frequency domain data in conjunction with first data from the data-generation device (925) to compute a maximum displacement (940) of a chest (911) of the person in cardiac distress (910). Tracking the displacement step over time yields the rate at which compressions are delivered.

The Added-push step (5127) includes activating the cuing device to send a recommendation to the rescuer (905) when the maximum displacement (940) of the chest (911) of the person in cardiac distress (910) is computed to be inadequate. The maximum displacement could be too shallow or too deep and the term "inadequate" is intended to mean both.

Figure 6:
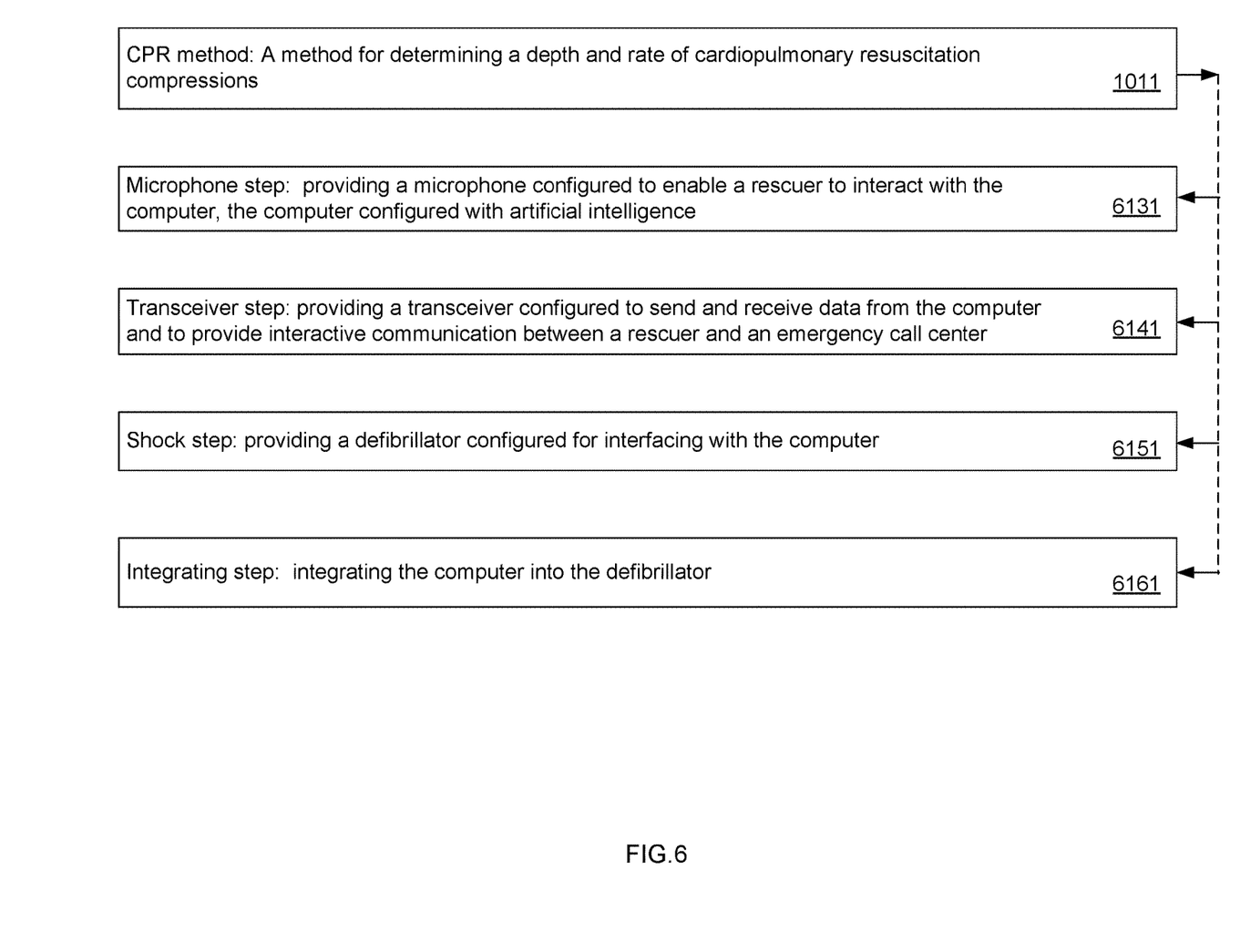
FIG. 6 is a chart illustrating optional added steps in the method.

The Microphone step (6131) includes providing a microphone (965) configured to enable the rescuer (905) to interact with the computer (915), the computer (915) configured with artificial intelligence.

The Transceiver step (6141) includes providing a transceiver (975) configured to send and receive data from the computer (915) and to provide interactive communication between the rescuer (905) and an emergency call center. The transceiver (975) is an electronic device which is a combination of a wireless transmitter and a receiver. The transceiver (975) can both transmit and receive electromagnetic waves using an antenna for communication purposes.

The Shock step (6151) includes providing a defibrillator (955) configured for interfacing with the computer (915); and The Safety step (6152) includes warning the rescuer (905) when the computer (915) determines that activation of the defibrillator (955) would be unsafe due to anyone in contact with the person in cardiac distress (910), or when the person in cardiac distress (910) is in water.

The Integrating step (6161) includes integrating the computer (915) into the defibrillator (955). This step is instructive in that, whenever practical, any component used in the method of the invention can be combined with any other component to perform multiple functions.

Figure 7:
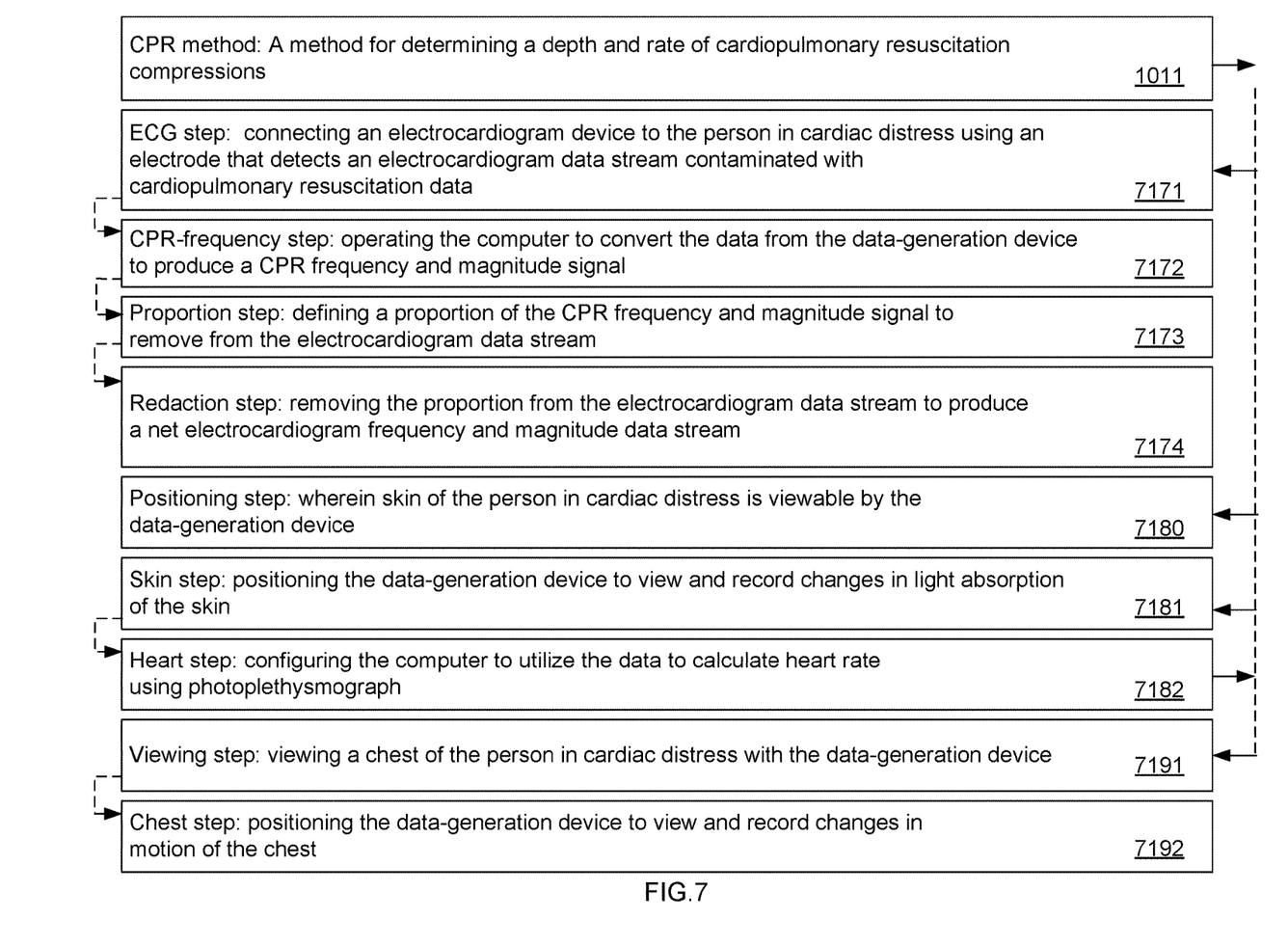
FIG. 7 is a chart illustrating optional added steps in the method.

The ECG step (7171) includes connecting an electrocardiogram (ECG) device to the person in cardiac distress (910) using an electrode that detects an electrocardiogram data stream contaminated with cardiopulmonary resuscitation data. An ECG device or machine can be equipped with 1 electrode or multiple electrodes. The electrocardiogram data stream reports on heart rhythm, which can include normal or abnormal rhythms, such as rhythms that are too slow (bradycardia) or rhythms that are too fast (tachycardia). Typically, heart rate and rhythm are both shown on an ECG strip or display, and the computer (915) is preferably configured to use either to analyze the heart activity of the person in cardiac distress (910).

The CPR-frequency step (7172) includes operating the computer (915) to convert the data from the data-generation device (925) to produce a CPR frequency and magnitude signal.

The Proportion step (7173) includes defining a proportion of the CPR frequency and magnitude signal to remove from the electrocardiogram data stream. The proportion is defined in advance of any treatments, as the frequency profile representing a typical CPR frequency that overlaps with a typical ECG signal.

The Redaction step (7174) includes removing the proportion from the electrocardiogram data stream to produce a net electrocardiogram frequency and magnitude data stream.

Positioning step (7180) requires that the data-generation device (925) be in a position where the skin of the person in cardiac distress is viewable by the data-generation device (925).

The Skin step (7181) includes positioning the data-generation device (925) to view and record changes in light absorption of the skin of the person in cardiac distress (910).

The Heart step (7182) includes configuring the computer (915) to utilize the data to calculate heart rate using photoplethysmography (PPG). Photoplethysmography is an optical technique used to detect volumetric changes in blood in peripheral circulation. A photoplethysmogram is an optically obtained plethysmogram that can be used to detect blood volume changes in the microvascular bed of tissue. A PPG is often obtained by using a pulse oximeter, which illuminates the skin and measures changes in light absorption.

The Viewing step (7191) includes viewing the chest (911) of the person in cardiac distress (910) with the data-generation device (925). Such monitoring of the chest helps to determine proper rescue ventilation and can be used to calculate respiration.

The Chest step (7192) includes positioning the data-generation device (925) to view and record changes in motion of the chest (911) of the person in cardiac distress (910).

Figure 8:
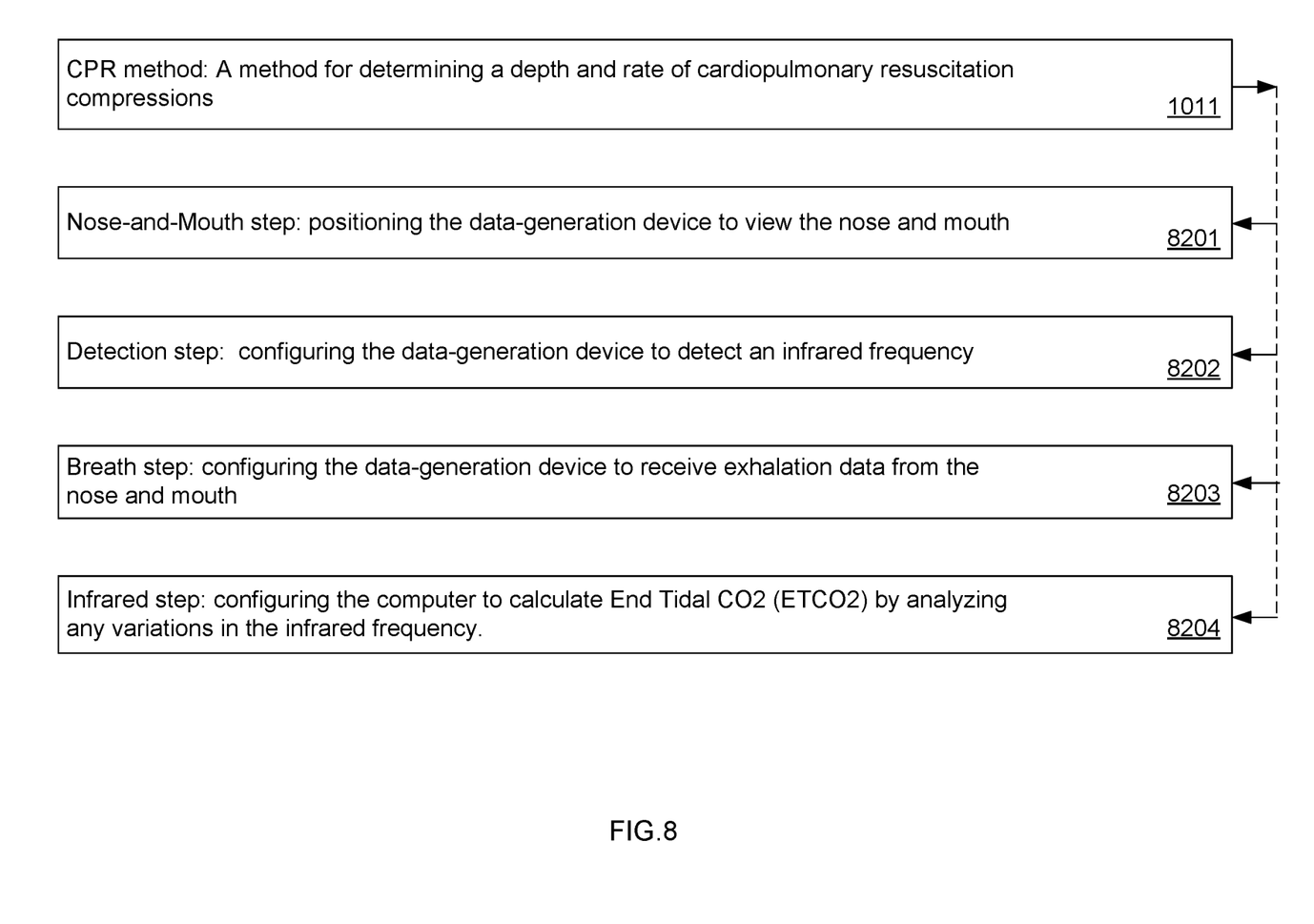
FIG. 8 is a chart illustrating optional added steps in the method.

The Nose-and-Mouth step (8201) includes positioning the data-generation device (925) to view the nose and mouth of the person in cardiac distress (910).

The Detection step (8202) includes configuring the data-generation device (925) to detect an infrared frequency.

The Breath step (8203) includes configuring the data-generation device (925) to receive exhalation data from the nose and mouth of the person in cardiac distress (910).

The Infrared step (8204) includes configuring the computer (915) to calculate End Tidal CO2 (ETCO2) by analyzing any variations in the infrared frequency. The study of carbon dioxide expiration is called capnometry and its graphical representation is called capnography. Capnography digitization can use image processing techniques to improve emergency cardiac treatment.

Example 1

In this example, the method first utilizes steps for determining the depth of compression of the chest of a person in cardiac distress, also referred to as a patient. This depth is calculated using two distances determined on the fly by the computer using data from a camera that is carried by a third person recording the scene.

The computer first calculates movement of an article that moves up and down with the chest of the patient undergoing CPR by a rescuer. The depth is calculated over time relative to a stationary feature located on the ground or near the patient. This calculation involves image analysis that enables determining the distance between the camera and the stationary feature and then determining the distance between the camera and the article. Once these distances are known, then a simple subtraction enables the determination of the depth of compression of the chest of the patient.

In this example 1, the computer uses the article and stationary features to calculate both the depth as well as the relative compression depth from front to back of the chest (i.e., anterior-posterior) dimension, cuing the rescuer to obtain a ⅓ depression if the patient is a child. The computer also prompts the rescuer to achieve full recoil if leaning on the patient is detected during CPR.

In this example, camera collects data on the frequency attributes of the CPR. Also, in this example, the patient is also hooked up to an ECG device that monitors the patient's heart and delivers an electrocardiogram for analysis. The ECG device utilizes one or more electrodes capable of detecting ECG signals during application of chest compressions.

In this example, the CPR compressions contaminate the ECG frequency data and the computer is then used to remove much of this contamination so that an ECG can be viewed without CPR artifacts.

Thus, in this example, the computer is used in real time for obtaining the ECG and redacting the CPR artifacts from the ECG signal. By knowing the CPR frequency by operating the computer for calculation of a movement of an article over time relative to a stationary feature, the computer is able to subtract some or all of the CPR frequency from the ECG signal, permitting evaluation of cleaned up ECG and CPR frequency data.

Example 2

In this second example, the method employs a computer capable of processing vision, a camera wirelessly connected to the computer, a device capable of providing visual cues, auditory cues and augmented reality of a scene with a person in need of cardiac rescue and a rescuer. In this second example the augmented reality glasses have an inertial measurement unit, an integrated camera, a computer, and a speaker. In this example 2, the augmented reality glasses draw virtual outlines for placement of a defibrillator pad.

Figure 9:
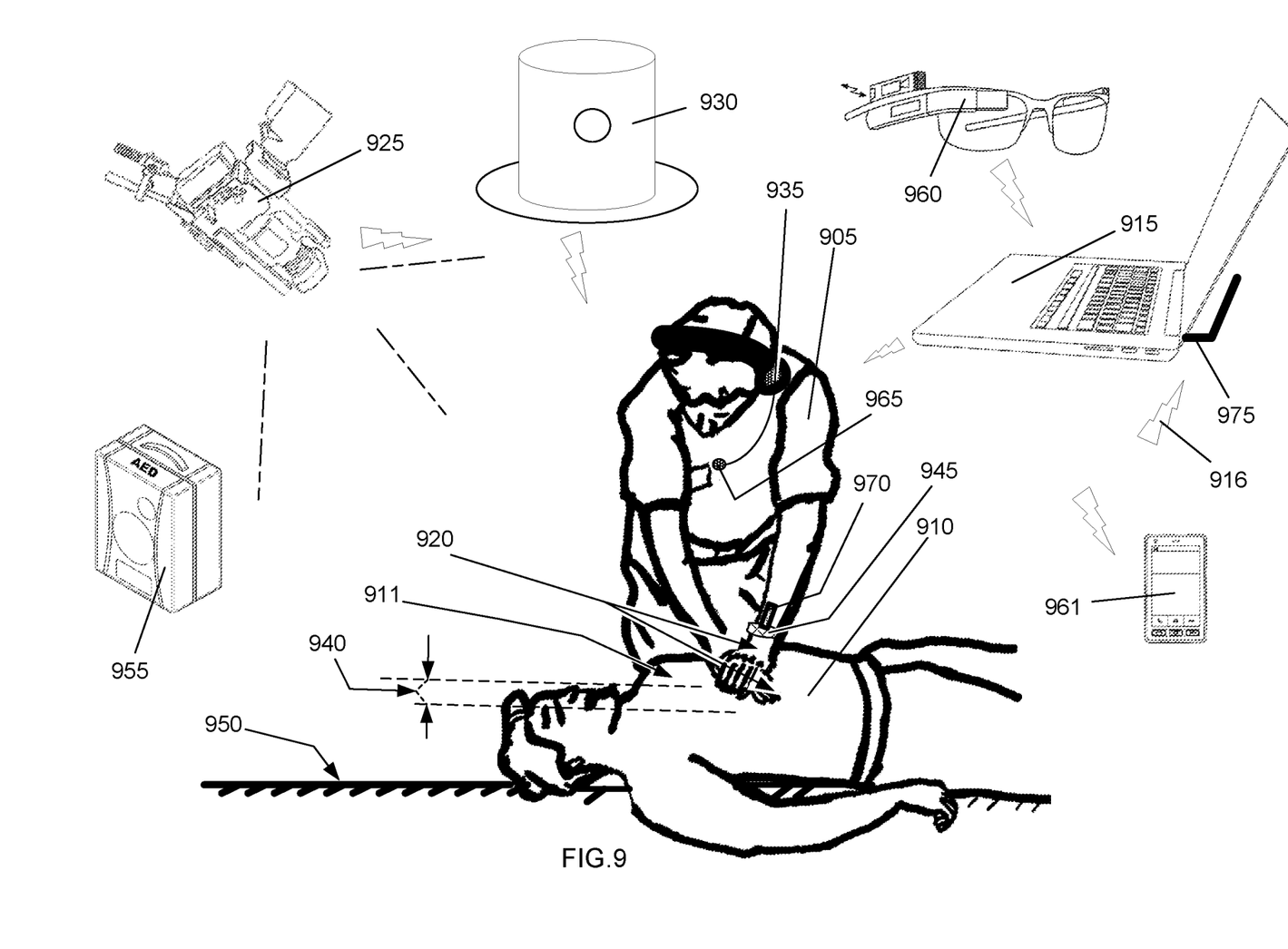
FIG. 9 is an illustration of a rescuer treating a person in cardiac distress.

In this second example, the method further employs a bracelet or wrist band which contains an image of known size that is used to determine the distance between the camera and rescuer's hands (920). The wrist band also contains an inertial measurement unit and a Global Positioning System (GPS) chip.

In this second example, the method further employs a stationary component, which is a small puck that sits on the ground next to the person in need of rescue. The puck has a known size and shape recognizable by the computer when viewed by the camera.

In this second example, the augmented reality glasses provide visual cues, auditory instructions, real time feedback, and augmented reality to the rescuer wearing the augmented reality glasses.

In this second example, a stationary GPS component is part of a defibrillator brought by the rescuer and is present at the scene.

In this second example a rescuer is called to the scene of a person in need of cardiac rescue who is lying on the ground.

The rescuer dons the augmented reality glasses, which assess the situation via computer vision. Using video and audio queues the computer instructs the rescuer to yell at the person and shake them: "Are you okay? ARE YOU OKAY"? The inertial measurement unit in the glasses tracks the motion of the camera attached to the rescuer.

When the person does not respond, the augmented reality glasses receive instructions from the computer and provide audio instructions to the rescuer to put on a wrist band.

The augmented reality glasses receive further audio for the rescuer to turn on the defibrillator. The computer next instructs the rescuer through the augmented reality glasses on what to do with real time feedback (e.g., placing pads, avoiding hazards etc.). This first instructions include CPR. CPR is the most complicated since the components must enable the computer to provide immediate feedback to the rescuer on rate, depth, and position. The computer is configured to tell the rescuer when to pause and when to resume CPR treatment.

The stationary feature, the puck, is on the ground next to the patient. The defibrillator may also double as a stationary component.

The computer sends instructions to the rescuer explaining the steps in implementing CPR. Through integration with the defibrillator, the computer tells the rescuer whether or not a shockable rhythm has been detected, whether or not to stop CPR, when to apply defibrillator pads, when to re-start CPR once pads are on, when to stop in order to shock, and when to start again. Using the camera, the computer confirms that no one is touching the patient before delivering any therapy and warns the rescuer if someone is touching the person in cardiac distress.

The computer assesses the visual data to determine the rate of CPR using the image of known size on the rescue bracelet and the stationary component. The computer assesses the change in height over time of the rescuer's hands (920) and is confirmed using the inertial measurement unit. Additionally, changes in height may be determined using a differential GPS between a GPS chip in the stationary puck and a GPS in the rescue bracelet.

CPR depth is calculated using an algorithm to combine the following calculations mathematically: Using only an inertial measurement unit on the bracelet the system measures the acceleration signal. This signal is then converted into the frequency domain through Fourier transforms. Using the frequency domain data, computer calculates average displacement without integration by modeling the displacement signal and computing the maximum displacement over the frequency.

The computer calculates where the rescuer's hands (920) are in space above the floor. The computer determines how far away the glasses, which have the camera incorporated therein, are from the person in cardiac distress by calibrating distance using the sensor in the bracelet and the stationary component. The computer determines the orientation of the rescuer's head using the inertial measurement unit built into the glasses.

The depth of the compression is computed by using differential GPS. Differential GPS uses data from the sensor in the wristband and stationary object. The computer then determines the Z axis motion.

The computer also determines the compression depth substituting vision for the GPS. By placing a puck or automated external defibrillator (AED) on the floor with an image of known size and within the line of sight of the camera in the augmented reality glasses, the computer: (1) computes the distance from the camera to stationary object then (2) computes the distance from the camera to the wristband. Subtracting those distances computes the height above the floor of the rescuer's hands (920) or patient's chest. Using the camera's video data, the computer calculates, and coaches the rescuer to perform CPR at the proper depth and rate. Essentially, computer vision is used to augment the differential GPS.

Third Example

In this third example, the method is utilized by an autonomous or semi-autonomous CPR robot that automates CPR for a patient (e.g., https://www.lucas-cpr.com/). Such a device would have a compression mechanism centered over the chest that could utilize the disclosed steps.

The steps for determining the depth of compression of the chest of a person in cardiac distress, also referred to as a patient. This depth is calculated using two distances determined on the fly by the computer using data from a camera located near the upper portion of the CPR device. It can be used to calibrate the compression device or to measure movement.

In this third example, the data generation device includes two stereo cameras and a time of flight device to detect the location of the patient's chest in space.

In this third example, the article is used to determine the correct placement in space for the compression device (e.g., on the breastbone, just below a patient's nipples).

In this third example, the computer first calculates movement or location of an article that moves up and down with the chest of the patient undergoing CPR by a device. The depth is calculated over time relative to a stationary feature located on a lower portion of the CPR device. If the cameras are mounted in a stationary position, these cameras also comprise a stationary feature. This calculation involves image analysis that enables determining the distance between the camera and the stationary feature and then determining the distance between the camera and the article, which might a defibrillation pad or sticker on the patient's chest or an image on the compression mechanism. In this instance, the article could also be pre-determined part of the patient's anatomy, such as a nipple. Once these distances are known, then a simple subtraction enables the determination of the depth of compression of the chest of the patient or the location of the compression mechanism.

In this third example, the computer uses the article and the stationary cameras to calculate the depth if the patient is an adult. If the patient is a child, the computer uses the stationary feature located on a lower portion of the CPR device to calculate relative compression depth from front to back of the chest (i.e., anterior-posterior) dimension, cuing the rescuer to obtain a ⅓ depression.

In this third example, the camera collects data on the frequency attributes of the CPR or the frequency is otherwise determined by the device itself. Also, in this example, the patient is also hooked up to an ECG device that monitors the pulse of the patient's heart and delivers an electrocardiogram for analysis. The ECG device utilizes one or more electrodes capable of detecting ECG signals during application of chest compressions.

In this third example, the CPR compressions ECG signals contaminate the ECG CPR frequency data and the computer is then used to remove much of this contamination.

Thus, in this third example, the computer is used in real time for obtaining the ECG and redacting the CPR artifacts from the ECG signal. By knowing the CPR frequency by operating the computer for calculation of a movement of an article over time relative to a stationary feature, the computer is able to subtract some or all of the CPR frequency from the ECG signal, permitting evaluation of cleaned up ECG and CPR frequency data.

In this third example, the camera attached to the CPR device is also used to obtain respiration when CPR is not active. The respiration is obtained via the data generation device.

In this third example, the camera attached to the CPR device is also used to obtain heart rate when CPR is not active. The heart rate is obtained via the data generation device.

In this third example, the camera attached to the CPR device is also used to measure $CO_2$ tidal volume to predict efficacy of resuscitation. The tidal volume is predicted via the data generation device.

The above-described embodiments including the drawings are examples of the invention and merely provide illustrations of the invention. Other embodiments will be obvious to those skilled in the art. Thus, the scope of the invention is determined by the appended claims and their legal equivalents rather than by the examples given.

INDUSTRIAL APPLICABILITY

The invention has application to the rescue industry.

What is claimed is:

1. A method for determining a depth and rate of cardiopulmonary resuscitation compressions, the method comprising the steps of:
   providing a computer, a stationary feature, a data-generation device, and an article;
   configuring the computer to receive data from the data-generation device;
   locating the data-generation device to view the stationary feature and the article;
   locating a person in cardiac distress lying on a surface;
   configuring a Z axis as a direction orthogonal to the surface;
   configuring the stationary feature as a fixed reference;
   configuring the article to be movable with a chest of the person in cardiac distress;
   configuring each of a plurality of coordinate systems to measure distance on the Z axis;
   configuring the data-generation device to be a frame of reference in the plurality of coordinate systems;
   viewing the article and the stationary feature with the data-generation device to generate the data sent to the computer; and
   operating the computer to perform a calculation of a movement of the article along the Z axis over time relative to the stationary feature, said calculation utilizing the computer to rotate, scale, and translate travel measurements between the plurality of coordinate systems, said calculation comprising a determination of a difference between a first distance and a second distance, said first distance defined by a first space between the data-generation device and the stationary feature on the Z axis, said second distance defined by a second space between the article and the data-generation device on the Z axis.

2. The method of claim 1, further comprising the steps of:
   selecting the stationary feature to comprise a defined plane of the surface;
   configuring a time-of-flight sensor as the data-generation device, the time-of-flight sensor configured to view the article and the defined plane;
   the data-generation device further comprising a camera, the camera configured to view the article; and configuring the time-of-flight sensor to project a virtual grid over the article, the person in cardiac distress and the defined plane.

3. The method of claim 2, further comprising the step of configuring the time-of-flight sensor to identify the defined plane by computing a two-dimensional surface that corresponds most closely to an outer edge of the virtual grid.

4. The method of claim 1, further comprising the steps of
configuring the stationary feature with a shape or image having a known dimension; and
calculating the first distance between the data-generation device and the stationary feature using the data and the known dimension of the stationary feature.

5. The method of claim 1, further comprising the steps of
configuring the article with a shape or image having a second known dimension; and
calculating the second distance between the data-generation device and the article using the data and the second known dimension.

6. The method of claim 1, further comprising the steps of:
recording an electrocardiogram from the operation of a defibrillator on the person in cardiac distress; and
recording the data from the data-generation device on a rate of cardiopulmonary resuscitation and depth of chest compression by a rescuer.

7. The method of claim 1, further comprising the steps of:
providing a cuing device;
configuring the cuing device to send guidance to a rescuer, the cuing device connected to the computer; and
activating the cuing device to send a recommendation to the rescuer when an adjustment of an action of the rescuer is suggested by the computer in treating the person in cardiac distress.

8. The method of claim 7, further comprising the step of providing augmented reality glasses configured to be part of the cuing device.

9. The method of claim 7, further comprising the step of sending the recommendation selected from the group consisting of a visual cue and an auditory cue.

10. The method of claim 7, further comprising the step of selecting the cuing device from the group consisting of a smartphone, a computer tablet, a laptop display, augmented reality glasses, a defibrillator, and augmented reality glasses equipped with an inertial measurement unit.

11. The method of claim 1, further comprising the step of defining the stationary feature to comprise a known dimension of a defibrillator.

12. The method of claim 1, further comprising the steps of:
including an inertial measurement unit in the article;
connecting the inertial measurement unit to the computer wherein the computer receives motion data from the inertial measurement unit indicating a measure of acceleration of motion of the article;
operating the computer to convert the motion data from the inertial measurement unit into frequency domain data through Fourier transforms;
using the frequency domain data in conjunction with first data from the data-generation device to compute a maximum displacement of a chest of the person in cardiac distress;
providing a cuing device;
configuring the cuing device to send guidance to a rescuer, the cuing device connected to the computer; and
activating the cuing device to send a recommendation to the rescuer when the maximum displacement of the chest of the person in cardiac distress is computed to be inadequate.

13. The method of claim 1, further comprising the step of providing a microphone configured to enable a rescuer to interact with the computer, the computer configured with artificial intelligence.

14. The method of claim 1, further comprising the step of providing a transceiver configured to send and receive data from the computer and to provide interactive communication between a rescuer and an emergency call center.

15. The method of claim 1, further comprising the step of providing a defibrillator configured for interfacing with the computer.

16. The method of claim 15, further comprising the step of integrating the computer into the defibrillator.

17. The method of claim 1, further comprising the steps of:
connecting an electrocardiogram device to the person in cardiac distress using an electrode that detects an electrocardiogram data stream contaminated with cardiopulmonary resuscitation data;
operating the computer to convert the data from the data-generation device to produce a CPR frequency and magnitude signal;
defining a proportion of the CPR frequency and magnitude signal to remove from the electrocardiogram data stream; and
removing the proportion from the electrocardiogram data stream to produce a net electrocardiogram frequency and magnitude data stream.

18. The method of claim 1, wherein skin of the person in cardiac distress is viewable by the data-generation device, the method further comprising the steps of:
positioning the data-generation device to view and record changes in light absorption of the skin; and
configuring the computer to utilize the data to calculate heart rate using photoplethysmography.

19. The method of claim 1, further comprising the steps of:
viewing a chest of the person in cardiac distress with the data-generation device; and
positioning the data-generation device to view and record changes in motion of the chest.

20. The method of claim 1, wherein a nose and mouth of the person in cardiac distress is viewable by the data-generation device, the method further comprising the steps of:
positioning the data-generation device to view the nose and mouth;
configuring the data-generation device to detect an infrared frequency;
further configuring the data-generation device to receive exhalation data from the nose and mouth; and
further configuring the computer to calculate End Tidal $CO_2$ (ETCO2) by analyzing any variations in the infrared frequency.

* * * * *